US00PP30968P2

(12) United States Plant Patent
Korlipara

(10) Patent No.: US PP30,968 P2
(45) Date of Patent: Oct. 22, 2019

(54) ***ARTEMISIA* PLANT NAMED 'TNARTMS'**

(50) Latin Name: *Artemisia mauiensis*
Varietal Denomination: TNARTMS

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,965

(22) Filed: May 29, 2018

(51) Int. Cl.
*A01H 5/12* (2018.01)
*A01H 6/14* (2018.01)

(52) U.S. Cl.
USPC ..... Plt./373

(58) Field of Classification Search
USPC ..... Plt./373, 263.1
CPC . A01H 5/12; A01H 5/025; A01H 5/02; A01H 5/00; A01H 6/14
See application file for complete search history.

(56) References Cited

PUBLICATIONS

Floral Daily 2018, US: "We were sold out within hours", retrieved on Apr. 11, 2019, retrieved from the Internet at https://www.floraldaily.com/article/9014002/us-we-were-sold-out-within-hours/, 3 pp. (Year: 2018).*

* cited by examiner

*Primary Examiner* — June Hwu
(74) *Attorney, Agent, or Firm* — Klarquist Sparkman, LLP

(57) ABSTRACT

A new and distinct *Artemisia* plant named 'TNARTMS' is characterized by excellent branching, a compact dense habit, and excellent vigor.

1 Drawing Sheet

Botanical denomination: *Artemisia mauiensis.*
Variety designation: 'TNARTMS'.
Trademark designation: Makana™ Silver.

BACKGROUND OF THE INVENTION

The present invention relates to a new and distinct cultivar of *Artemisia mauiensis* and given the cultivar name 'TNARTMS'. *Artemisia* is in the family Asteraceae. The new cultivar is part of a planned breeding program for the landscape with mounding, compact habits resulting as a small shrub. The new cultivar is a whole plant mutation of *Artemisia mauiensis* which was discovered in tissue culture in Canby, Oreg.

Compared to the species, *Artemisia mauiensis*, the new cultivar has better branching, and a larger denser habit giving it a fuller appearance.

This new *Artemisia* cultivar is uniquely distinguished by:
1. excellent branching,
2. compact, dense habit, and
3. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar as four-month-old plant growing outside in full sun in late August in Canby, Oreg.

FIG. 2 shows the flowers of *Artemisia* 'TNARTMS' as an eight-month-old growing in a gallon pot in a greenhouse during December in Canby, Oreg.

DETAILED PLANT DESCRIPTION

The following is a detailed description of the new *Artemisia* cultivar based on observations of eight-month-old specimen growing in gallon pots in a greenhouse during December in Canby, Oreg. Canby is in Zone 8 on the USDA Hardiness map. Temperatures range from an average high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type.*—Subshrub.

*Hardiness.*—USDA Zones 9 to 11.

*Size.*—Grows to about 77 cm wide and 42 cm tall.

*Form.*—Small shrub.

*Stem.*—Grows to 13 mm wide and 32 cm long with internodes to 1 cm long; usually one main woody stem from base with about 18 branches up the main stem, about 13 secondary stems from the base; tomentose hairs on the top half of all branches, base Greyed Brown N199A on lower end of stem blending to Greyed Green 192B.

*Vigor*.—Excellent.

*Roots*.—Fibrous, with many downward growing and few laterals, ivory in color, Yellow White 158D, roots develop easily from cuttings from the crown.

Leaf:

*Aromatic*.—Yes.

*Type*.—Tripinnatifid, with filiform leaf segments.

*Shape*.—Ovate to deltoid in outline, with pinnae and pinnules linear.

*Arrangement*.—Alternate.

*Blade size*.—Grows to 9 cm long and 10 cm wide, leaflets up to 5 cm long and 4 cm wide.

*Margins*.—Entire.

*Apex*.—Acute.

*Base*.—Cordate in outline.

*Surface texture*.—Both sides tomentose.

*Venation*.—Pinnate, veins not prominent, Greyed Green 189C.

*Rachis color*.—Greyed Green 192B.

*Leaf color*.—Both sides closest to Greyed Green 189C.

*Petiole description*.—Grows to 3.5 cm long and 2 mm wide, tomentose, Greyed Green 192B.

Inflorescence:

*Type*.—Composite heads in a raceme-like arrangement on terminal and lateral stems, all branches become flowering at ends.

*Number of flowering stems*.—About 120.

*Strength*.—Weak.

*Raceme-like stem*.—Grows to 5 mm long and 2.5 cm wide with about 50 inflorescences per stem, to 2 mm wide, tomentose, Greyed Green 192B, leafy throughout, leaves pinnate to linear (4.5 cm long less than 1 mm wide) in filiform segments.

*Form*.—Disc florets only; nodding.

*Immature inflorescence* (*bud*).—3 mm wide and 2 mm deep.

*Ray florets*.—Absent.

*Disc*.—Flat becoming slightly conic, becoming 4 mm deep and 5 mm wide with maturity, Yellow 2B.

*Disc florets*.—About 80 in number, each with 1 pistil and 5 stamen, grow to 3 mm long and 0.5 mm wide, corolla 2 mm long and 0.5 mm wide, tubular, 5 lobed, glabrous, Green Yellow 1B; pistil 1.5 mm long, ovary 1 mm long and 0.5 mm wide, Yellow Green 1B, style 1 mm long, stigma and style Green Yellow 1C; stamens 0.5 mm long, Green Yellow 1C overall, filaments 0.2 mm long, Y, anthers 0.3 mm long, pollen Yellow 2B.

*Phyllaries*.—About 30, grow to 2 mm long and 1 mm wide, ovate, between Green 138B and Green 138C margins entire, tip acute, tomentose on back side, glabrous inside.

*Receptacle*.—Ovoid, grows to 1 mm wide and 1.5 mm deep, Green 143B.

*Bloom period*.—About 10 weeks, late summer in Maui, Hi.

*Fragrance*.—Slight.

*Lastingness*.—Each inflorescence lasts about three weeks in Canby, Oreg.

Seeds: None seen.

*Fertility*.—Unknown.

Disease and pests: No pests or diseases have been observed on plants grown under commercial conditions in Canby, Oreg. No resistances are known.

I claim:

1. A new and distinct *Artemisia* plant as herein illustrated and described.

* * * * *

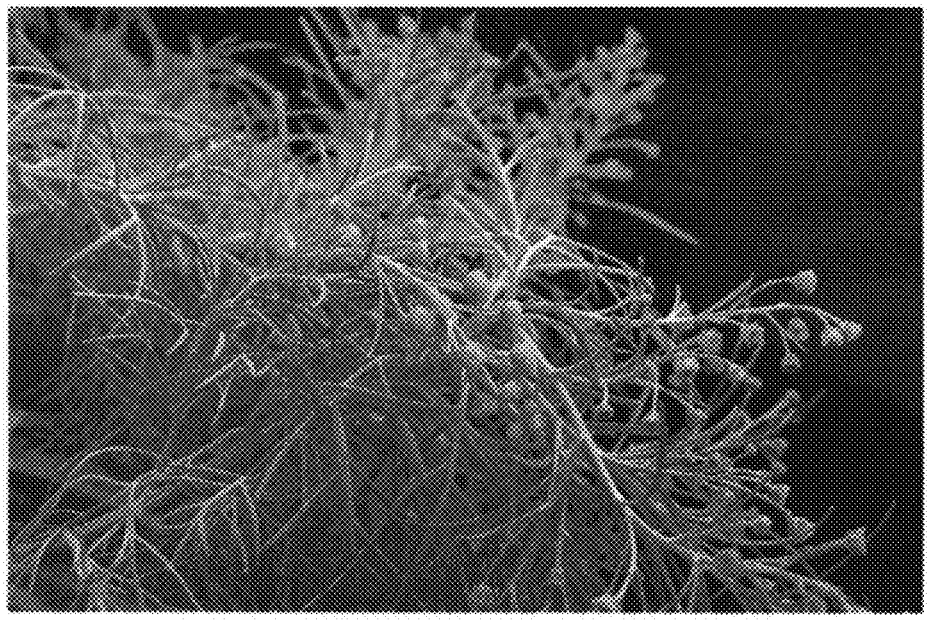

FIG. 1 Below
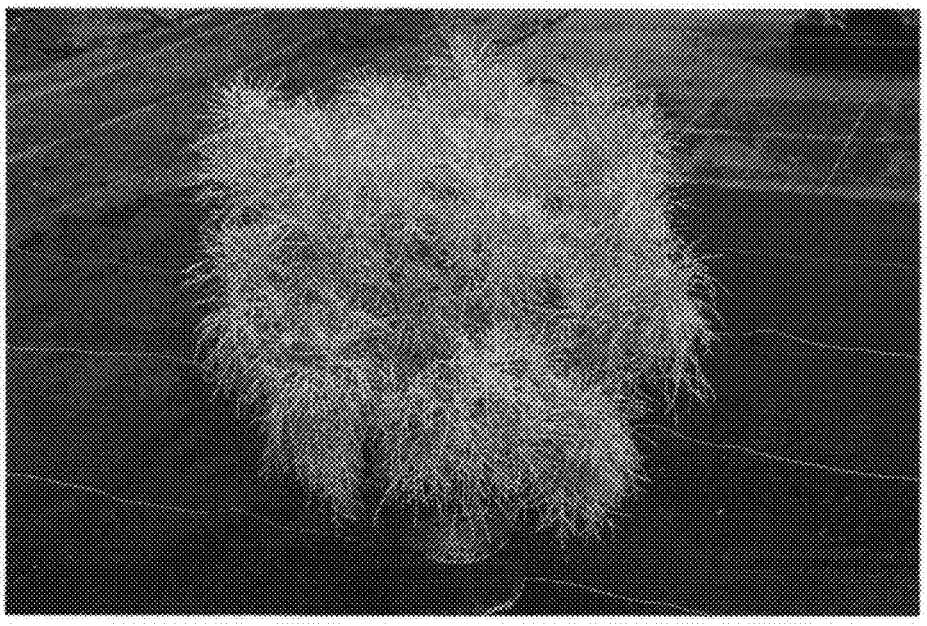
FIG. 2 Below